United States Patent [19]

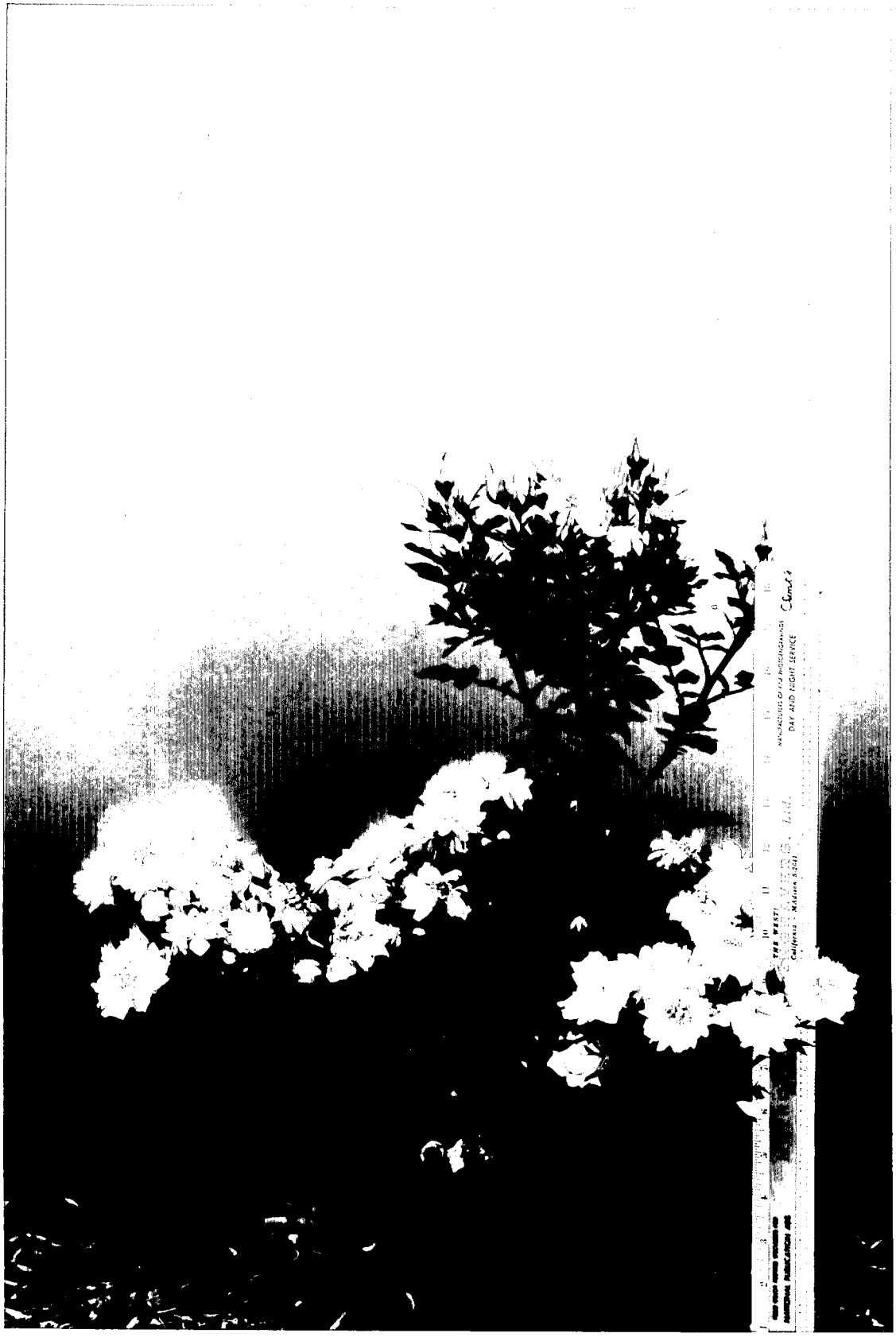
THE WEST
DAY AND NIGHT SERVICE

Warriner

[11] Patent Number: Plant 5,577

[45] Date of Patent: Oct. 29, 1985

[54] ROSE PLANT JACSMI

[75] Inventor: William A. Warriner, Tustin, Calif.

[73] Assignee: Jackson & Perkins Company, Medford, Oreg.

[21] Appl. No.: 549,298

[22] Filed: Nov. 7, 1983

[51] Int. Cl.[4] ..... A01H 5/00

[52] U.S. Cl. ..... Plt./8

[58] Field of Search ..... Plt./8

*Primary Examiner*—James R. Feyrer

*Attorney, Agent, or Firm*—Klarquist, Sparkman, Campbell, Leigh & Whinston

[57] ABSTRACT

A miniature rose variety having dwarf growth habit, large clusters of blooms with yellow petals numbering up to 75, resistance to rose powdery mildew, and light fragrance.

1 Drawing Figure

This present invention relates to a new and distinct variety of rose plant of the miniature class which was originated by me by crossing the variety Spanish Sun, U.S. Plant Pat. No. 2,809, with the variety Calgold, U.S. Plant Pat. No. 4,230.

The primary objective of this breeding was to produce a new miniature rose variety producing very double, small yellow flowers, borne heavily in clusters. This objective was substantially achieved along with other desirable improvements as evidenced by the following unique combination of characteristics which are outstanding in the new variety and which distinguish it from its parents, as well as from all other varieties of which I am aware:

1. A dwarf habit of growth, reaching a height of less than 24".
2. Large clusters of blooms.
3. Petal count up to 75.
4. Pure yellow petal color.
5. Good resistance to rose powdery mildew.
6. Light fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Spanish Sun, U.S. Plant Pat. No. 2,809.

*Pollen parent.*—Calgold, U.S. Plant Pat. No. 4,230.

Classification:

*Botanical.*—Rosa hybrid.

*Commercial.*—Miniature.

FLOWER

Observations made from specimens grown in August at Irvine, Calif.

Blooming habit: Recurrent, continuous.

Bud:

*Size.*—$\frac{1}{2}$" when petals start to unfurl.

*Form.*—Blunt top, ovoid.

*Color.*—When sepals first divide, Near Yellow 13A. When half blown; upper side of petals Yellow 13A with lighter petal tips to 13D; lower side of petals Yellow 13A with lighter petal tips to 13D.

*Sepals.*—Color: Outer surface Green 138B with smooth surface. Three appendaged sepals lightly appendaged. Two unappendaged sepals hairy edged and glandular.

*Receptacle.*—Color: Green 138B. Shape: Funnel. Size: Small. Surface: Slightly hairy.

*Peduncle.*—Length: Short. Surface: Covered with very short pubescence and a few stipitate glands. Color: Light green. Strength: Stiff, erect.

*Opening.*—Petals gradually fold out to a recurved form in full open stage.

Bloom:

*Size.*—Small. Average open size: $1\frac{1}{4}$" to $1\frac{1}{2}$".

*Borne.*—In clusters, irregular.

*Stems.*—Short, strong.

*Form.*—When first open, cupped. Permanence: Outer petals curl back.

*Petalage.*—Number of petals under normal conditions: 75.

*Color.*—Center of flower: Upper side of petals Yellow 13A; outer edge sometimes fades to Yellow 13D; reverse side of petals Yellow 13A; base of petals Yellow 13A. General tonality from a distance Yellow 13A.

*Variegations.*—None.

*Discoloration.*—General tonality at end of first day: No change. Third day: No change, Yellow 13A.

*Fragrance.*—Slight.

Petals:

*Texture.*—Thin.

*Shape.*—Outer petals are obovate, center petals are more narrow to oblanceolate.

*Form.*—Edges slightly quilled.

*Arrangement.*—Imbricated. Petaloids in center, many.

*Persistence.*—Drop off cleanly, hang on and dry occasionally.

*Lastingness.*—On the plant, long. As cut flower, long.

Reproductive parts:

*Anthers.*—Small, few, often coalesced with petaloids. Color: Yellow. Arrangement: Mixed with petaloids.

*Filaments.*—Color: Yellow.

*Styles.*—Color: Reddish.

PLANT

Form: Bush.

Growth: Vigorous, dwarf, upright. Mostly under 24" in height.

Foliage: Number of leaflets on normal mid-stem leaves: 5 or 7.

*Size.*—Small.

*Quantity.*—Normal.

*Color.*—New foliage: Green 137C. Old foliage: Green 137A.

Leaflets:

*Shape.*—Oval pointed.

*Texture.*—Upper side: Smooth.

*Edge.*—Serrated.

*Serration.*—Single, small.

*Petiole.*—Rachis: Color: Green. Underside: Prickles, stipitate glands on upper edge.

*Stipules.*—Long.

*Disease resistance.*—Resistant to mildew, blackspot under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, ordinary. On laterals from stalk, ordinary.

*Form.*—Long, straight.

*Color when young.*—Green.

*Position.*—Irregular.

Small prickles:

*Quantity.*—On main stalks, none. On laterals, none.

I claim:

1. A new and distinct variety of rose plant of the miniature class, substantially as herein shown and described, characterized particularly as to novelty by the unique combination of its dwarf plant, resistance to rose powdery mildew, short yellow buds and very double yellow flowers.

* * * * *